United States Patent [19]

Epple et al.

[11] 4,154,747

[45] May 15, 1979

[54] PRODUCTION OF VIRTUALLY PURE 1-AMINO-8-NITRO-4,5-DIHYDROXYANTHRAQUINONE

[75] Inventors: Gerhard Epple, Weisenheim; Wolfgang Elser, Wachenheim; Walter Himmele, Walldorf, all of Fed. Rep. of Germany

[73] Assignee: BASF Aktiengesellschaft, Ludwigshafen, Fed. Rep. of Germany

[21] Appl. No.: 917,252

[22] Filed: Jun. 20, 1978

[30] Foreign Application Priority Data

Jul. 7, 1977 [DE] Fed. Rep. of Germany ....... 2730720

[51] Int. Cl.$^2$ ............................................. C09C 97/26
[52] U.S. Cl. ................................. 260/380; 260/689
[58] Field of Search .......................... 260/380, 689

[56] References Cited

U.S. PATENT DOCUMENTS

| | | | |
|---|---|---|---|
| 2,068,371 | 1/1937 | Buxbaum | 260/380 |
| 2,684,359 | 7/1954 | Sogn | 260/689 |
| 3,060,200 | 10/1962 | Buecheler | 260/380 |
| 4,048,199 | 9/1977 | Elser et al. | 260/380 |

FOREIGN PATENT DOCUMENTS

2531259  2/1976  Fed. Rep. of Germany.

Primary Examiner—Allen B. Curtis
Assistant Examiner—Raymond Covington
Attorney, Agent, or Firm—Oblon, Fisher, Spivak, McClelland & Maier

[57] ABSTRACT

A process for the preparation of 1-amino-8-nitro-4,5-dihydroxyanthraquinone by partially reducing the corresponding dinitrohydroxyanthraquinone and isolating the reduction product, in which crude 1,8-dinitro-4,5-dihydroxyanthraquinone obtained by nitrating 4,5-dihydroxyanthraquinone is partially reduced in a phenol-water mixture, which contains from 5 to 50% by weight of water, in the presence of an alkali metal phenolate, by means of a reductone, reductonate or a mixture of these. The product is virtually free from by-products and is suitable for use for the synthesis of dyes.

7 Claims, No Drawings

PRODUCTION OF VIRTUALLY PURE 1-AMINO-8-NITRO-4,5-DIHYDROXYAN-THRAQUINONE

The present invention relates to a process for the production of virtually pure 1-amino-8-nitro-4,5-dihydroxyanthraquinone by partially reducing 1,8-dinitro-4,5-dihydroxyanthraquinone.

Swiss Pat. No. 370,857 discloses that dinitro-dihydroxyanthraquinones can be reduced in an alkaline aqueous medium by means of sodium bisulfide or by means of a reducing sugar, eg. glucose. German Laid-Open Applications DOS Nos. 2,428,338 and 2,428,452 disclose the partial reduction of dinitro-dihydroxyanthraquinone with hydrazine in an aqueous medium or in an organic protic solvent.

A 1-amino-8-nitro-4,5-dihydroxyanthraquinone which may be used for the preparation of valuable dyes, eg. of the blue dyes described in German Laid-Open Application DOS No. 2,029,793, is only obtainable by the processes of the prior art by using pure 1,8-dinitro-4,5-dihydroxyanthraquinone, free from β-nitro compounds, as the starting material. According to the prior art, such a starting material can only be obtained as follows: 4,5-dichloro- or 4,5-dinitro-anthraquinone is reacted with phenol to give 4,5-diphenoxyanthraquinone. Nitration of this compound gives 1,8-dinitro-4,5-bis-(2',4'-dinitro-phenoxy)-anthraquinone, which is converted by alkaline scission into the disodium salt of 1,8-dinitro-4,5-dihydroxy-anthraquinone which is finally acidified to give 1,8-dinitro-4,5-dihydroxyanthraquinone, hereinafter also referred to as dinitrochrysazine (Endeavour 35, (September 1976), 137).

It is an object of the present invention to provide a process which is reliable in industrial operation and which may be used to prepare 1-amino-8-nitro-4,5-dihydroxyanthraquinone suitable for dye syntheses, ie. virtually pure 1-amino-8-nitro-4,5-dihydroxyanthraquinone, from the crude dinitrochrysazine obtainable by direct nitration of 4,5-dihydroxyanthraquinone (= chrysazine).

We have found that virtually pure 1-amino-8-nitro-4,5-dihydroxyanthraquinone can be obtained by partially reducing 1,8-dinitro-4,5-dihydroxyanthraquinone if crude 1,8-dinitro-4,5-dihydroxyanthraquinone obtained by nitration of 4,5-dihydroxyanthraquinone is partially reduced in a phenol-water mixture, which contains from 5 to 50 percent by weight of water, in the presence of an alkali metal phenolate, by means of a reductone, reductonate or a mixture of these.

Using the process of the invention, the crude 1,8-dinitro-4,5-dihydroxyanthraquinone obtainable by nitration of 4,5-dihydroxyanthraquinone is converted to a 1-amino-8-nitro-4,5-dihydroxyanthraquinone which according to chromatography is virtually pure and which is exceptionally suitable for the preparation of dyes. It is surprising that in the process according to the invention the by-products formed during the nitration, and/or the reduction products obtained therefrom, are selectively and virtually completely separated from the desired 1-amino-8-nitro-4,5-dihydroxyanthraquinone.

The economic advantage of the process according to the invention is that instead of the pure dinitrochrysazine, obtainable by an expensive synthesis entailing several stages, the crude dinitrochrysazine obtainable by direct nitration of chrysazine can be used for the partial reduction.

The process of the invention is in general carried out as follows: the crude dinitrochrysazine is suspended in phenol and water. The alkali metal phenolate is then either added as such or, advantageously, is produced in situ by adding an alkali metal hydroxide or alkali metal carbonate. The reducing agent is then added at from 20° to 100° C., whilst stirring, and the reaction mixture is kept at the desired temperature until no dinitrochrysazine is left. After the reaction mixture has cooled, it is filtered and the filter cake is washed with methanol and/or with dilute sodium carbonate solution until free from phenol, washed with water, if desired, and then dried.

The reaction medium used is a mixture of phenol and water. It contains from 5 to 50 percent by weight of water, preferably from 30 to 45 percent by weight, based on the mixture. The suspension of the crude dinitrochrysazine may advantageously be obtained by adding the crude dinitrochrysazine, in the form of an aqueous filter cake, to the phenol. If necessary, further phenol is then added so as to bring the water content in the phenol/water mixture to below 50 percent by weight, or water is distilled off as an azeotropic mixture with phenol or with another entraining agent.

The amount of reaction medium is in general from 2 to 10 times, preferably from 3 to 6 times, the amount of crude dinitrochrysazine employed. Its amount depends both on the phenol content and on the content of by-products in the crude dinitrochrysazine. As the phenol content increases, the amount of reaction medium can be reduced, whilst higher contents of impurities require an increase of from 10 to 25% in the amount of reaction medium.

As a rule, from 0.2 to about 1.5 moles of phenolate are employed per mole of dinitro-dihydroxyanthraquinone, the amount depending on the water content of the reaction medium and on the nature and amount of the reducing agent.

The reducing agents used in the process of the invention are selected from the group comprising the reductones and/or reductonates. Examples of suitable compounds are hydroxyacetone, dihydroxyacetone, glycolaldehyde, dihydroxybutanone, triose-reductone (2,3-dihydroxyacrylaldehyde), ascorbic acid, reductic acid (= cyclopentenediolone) and α-hydroxybutan-2-one. Triose-reductone and reductic acid are formed on acid or alkaline degradation of saccharides, eg. glucose or starch, or of molasses.

The amount of reducing agent required for the partial reduction depends on the nature of the reducing agent and on the reduction conditions.

Advantageously, the required amount of reducing agent is established by experiments under the reaction conditions to be employed subsequently. In these experiments, samples of the reaction product are examined chromatographically to ascertain what amount of reducing agent is required to ensure that all the dinitrochrysazine has disappeared.

For economic reasons, preferred reducing agents are dihydroxyacetone and especially hydroxyacetone and glucose. Technical-grade hydroxyacetone which still contains propylene glycol can be used.

The reduction is in general carried out at from room temperature (20° C.) to 100° C., preferably from 80° to 100° C., especially at the boiling point of the phenol-water mixture.

The reduction is as a rule complete in from 0.5 to 3 hours, depending on the conditions. It is regarded as complete when dinitrochrysazine is no longer detectable in a sample; further reducing agent and, if necessary, also alkali metal hydroxide for forming the phenolate may or may not be added to the reaction mixture during the reaction.

Using the above process, virtually pure 1-amino-8-nitro-4,5-dihydroxyanthraquinone is obtained from crude dinitrochrysazine which in turn is obtained by direct nitration of chrysazine. The product is suitable for all applications.

The Examples which follow illustrate the process of the invention. Parts and percentages are by weight.

EXAMPLE 1

498 parts of an aqueous filter cake of crude dinitrochrysazine (containing 33.1% of the latter, corresponding approximately to 165 parts of dry material), 550 parts of phenol and 32.5 parts of 50% strength sodium hydroxide solution are mixed and heated at 90° – 95° C. 100 parts of crude (78% strength) hydroxyacetone are added dropwise in the course of half an hour, whilst stirring. The reaction mixture is then refluxed for 1.5 hours. When it has cooled, the reaction product which has precipitated is filtered off and the filter residue is washed with 1,000 parts of 2% strength sodium carbonate solution and with hot water, and dried. 109 parts of 1-amino-8-nitro-4,5-dihydroxyanthraquinone, which appears pure according to thin layer chromatography, are obtained.

The crude dinitrochrysazine used as the starting material was prepared as follows:

4,000 parts of 23% strength oleum and 248 parts of boric acid are heated for 1 hour at 50° C., whilst stirring. When the mixture has cooled to 30° C., 360 parts of chrysazine (calculated as 100% pure) in the form of about 400 parts of 90% pure material are introduced at a rate such that the temperature does not rise above 50° C. The mixture is then heated for 2 hours at 50° C. and is cooled to 0° C., and 528 kg of mixed acid (containing 48% of $HNO_3$) are added dropwise in the course of 3 hours whilst cooling at 0°–5° C. by means of brine. After completion of the dropwise addition, the mixture is poured out onto ice water and the reaction product which precipitates is filtered off and washed neutral with water. Yield: 528 parts (calculated as dry material) of crude dinitrochrysazine, in the form of the aqueous filter cake having a solids content of 33.1%.

EXAMPLE 2

472 parts of an aqueous filter cake of crude dinitrochrysazine (containing 35.2% of the latter, corresponding to 165 parts of dry material), 550 parts of phenol and 40 parts of 50% strength sodium hydroxide solution are heated at 95°–100° C. whilst stirring. At this temperature, 111 parts of hydroxyacetone (about 98% pure) are added in the course of half an hour and the mixture is then refluxed for 1 hour. When it has cooled, the reaction product which has precipitated is filtered off and is washed with 500 parts of 2% strength sodium carbonate solution and with hot water. After drying, 111 parts of 1-amino-8-nitro-4,5-dihydroxyanthraquinone, which still contains small amounts of by-products, are obtained.

EXAMPLE 3

50 parts of an aqueous filter cake of crude dinitrochrysazine (containing 33.1% of the latter, corresponding to 16.5 parts of dry material), 60 parts of phenol and 3.24 parts of 50% strength sodium hydroxide solution are heated at 90°–100° C. 10 parts of dihydroxyacetone are introduced in the course of half an hour, whilst stirring. To complete the reaction, the mixture is then refluxed for 1.5 hours; it is then cooled and the reaction product which has precipitated is filtered off and is worked up as described in Example 1. After drying, 9.8 parts of chromatographically pure 1-amino-8-nitro-4,5-dihydroxyanthraquinone are obtained.

EXAMPLE 4

50 parts of an aqueous filter cake of crude dinitrochrysazine (containing 33.1% of the latter, corresponding to 16.5 parts of dry material) prepared as described in Example 1 b), 60 parts of phenol and 3.24 parts of 50% strength sodium hydroxide solution are heated at 90°–100° C. 14.85 parts of glucose are introduced in the course of half an hour. After stirring for 1 hour at 100° C., a further 3.24 parts of 50% strength sodium hydroxide solution are added. To complete the reaction, the mixture is then refluxed for 1 hour, after which it is worked up as described in Example 1. 8.3 parts of chromatographically virtually pure 1-amino-8-nitro-4,5-dihydroxyanthraquinone are obtained.

EXAMPLE 5

50 parts of an aqueous filter cake of crude dinitrochrysazine (containing 33.1% of the latter, corresponding approximately to 16.5 parts of dry material), 60 parts of phenol and 5.5 parts of anhydrous potassium carbonate are heated at 90°–95° C. 10 parts of hydroxyacetone are added dropwise in the course of half an hour, whilst stirring. The reaction mixture is refluxed for 3 hours and is then cooled, and the reaction product which has precipitated is filtered off. The filter residue is washed with 500 parts of 2% strength sodium carbonate solution and with hot water, and is dried. 11.0 parts of 1-amino-8-nitro-4,5-dihydroxyanthraquinone, which contains only traces of impurities, are obtained.

EXAMPLE 6

The procedure described in Example 5 is followed, but using 4.25 parts of anhydrous sodium carbonate instead of 5.5 parts of potassium carbonate. 10.3 parts of chromatographically virtually pure 1-amino-8-nitro-4,5-dihydroxyanthraquinone are obtained.

We claim:

1. In a process for the production of virtually pure 1-amino-8-nitro-4,5-dihydroxyanthraquinone by partially reducing 1,8-dinitro-4,5-dihydroxyanthraquinone in an aqueous medium and isolating the resultant 1-amino-8-nitro-4,5-dihydroxyanthraquinone, the improvement wherein crude 1,8-dinitro-4,5-dihydroxyanthraquinone obtained by nitration of 4,5-dihydroxyanthraquinone is partially reduced in a phenol-water mixture, which contains from 5 to 50% by weight of water, in the presence of an alkali metal phenolate by means of a reducing agent selected from the group consisting of a reductone, a reductonate and a mixture thereof.

2. A process as claimed in claim 1, wherein hydroxyacetone, dihydroxyacetone or glucose is used as the reducing agent.

3. A process as claimed in claim 1, wherein the reduction is carried out at from 20° C. to 100° C.

4. A process as claimed in claim 1, wherein the reduction is carried out at from 80° to 100° C.

5. A process as claimed in claim 1, wherein the reduction is carried out in the presence of from 0.2 to 1.5 moles of an alkali metal phenolate per mole of dinitrodihydroxyanthraquinone.

6. A process as claimed in claim 1, wherein the reduction is carried out in a phenol-water mixture which contains from 30 to 45% by weight of water.

7. A process as claimed in claim 2, wherein the amount of reducing agent used is such that no 1,8-dinitro-4,5-dihydroxyanthraquinone remains in the reaction mixture.

* * * * *